US009863942B2

(12) United States Patent
Hodges et al.

(10) Patent No.: US 9,863,942 B2
(45) Date of Patent: Jan. 9, 2018

(54) BIOSENSOR APPARATUS AND METHODS OF USE

(75) Inventors: Alastair McIndoe Hodges, Victoria (AU); Ronald Chatelier, Bayswater (AU); Dennis Rylatt, Wheelers Hill (AU)

(73) Assignee: Universal Biosensors Pty Ltd, Rowville, Victoria (AU)

(*) Notice: Subject to any disclaimer, the term of this patent is extended or adjusted under 35 U.S.C. 154(b) by 1119 days.

(21) Appl. No.: 12/563,091

(22) Filed: Sep. 18, 2009

(65) Prior Publication Data

US 2010/0006452 A1    Jan. 14, 2010

Related U.S. Application Data

(60) Division of application No. 11/284,097, filed on Nov. 21, 2005, now abandoned, which is a continuation-in-part of application No. 10/830,841, filed on Apr. 22, 2004, now Pat. No. 8,685,714, which is a continuation-in-part of application No. 10/105,050, filed on Mar. 21, 2002, now abandoned.

(51) Int. Cl.
*G01N 33/53* (2006.01)
*G01N 33/543* (2006.01)

(52) U.S. Cl.
CPC ......... *G01N 33/5438* (2013.01); *G01N 33/53* (2013.01); *G01N 33/543* (2013.01); *G01N 33/54326* (2013.01); *Y10T 29/49124* (2015.01)

(58) Field of Classification Search
CPC .......... G01N 33/54326; G01N 33/5438; Y10T 29/49124
USPC ................................................ 436/518, 526
See application file for complete search history.

(56) References Cited

U.S. PATENT DOCUMENTS

| 3,552,928 A | 1/1971 | Fetter et al. |
| 4,053,381 A | 10/1977 | Hamblen et al. |
| 4,076,596 A | 2/1978 | Connery et al. |
| 4,125,372 A | 11/1978 | Kawai et al. |

(Continued)

FOREIGN PATENT DOCUMENTS

| AU | 3104293 | 7/1993 |
| AU | 5487394 | 8/1994 |

(Continued)

OTHER PUBLICATIONS

Chinese Intellectual Property Office, First Office Action in corresponding Chinese Patent Application No. 200610149310.5, dated Mar. 10, 2011, 3 pages.

(Continued)

*Primary Examiner* — Erik B Crawford
(74) *Attorney, Agent, or Firm* — Hahn Loeser & Parks LLP (57) ABSTRACT

Disclosed herein are methods and devices for detecting the presence of an analyte of interest. A biosensor device can include a reaction chamber and an electrochemical detection chamber. The reaction chamber can include at least one immobilized binding site and a probe conjugate adapted to bind to at least one of the target analyte and the immobilized binding site while the detection chamber can include electrodes for detecting an electrochemical reaction. If present, the target analyte in the fluid sample results in a change in the amount of probe conjugate bound in the reaction chamber, which can be detected electrochemically in the detection chamber.

24 Claims, 4 Drawing Sheets

(56) References Cited

U.S. PATENT DOCUMENTS

| | | | |
|---|---|---|---|
| 4,168,146 A | 9/1979 | Grubb et al. | |
| 4,224,125 A | 9/1980 | Nakamura et al. | |
| 4,225,557 A | 9/1980 | Hartl et al. | |
| 4,298,011 A | 11/1981 | Mangurten et al. | |
| 4,301,412 A | 11/1981 | Hill et al. | |
| 4,301,414 A | 11/1981 | Hill et al. | |
| 4,319,969 A | 3/1982 | Oda et al. | |
| 4,323,536 A | 4/1982 | Columbus | |
| 4,374,013 A | 2/1983 | Enfors et al. | |
| 4,376,825 A | 3/1983 | Rubenstein et al. | |
| 4,404,066 A | 9/1983 | Johnson | |
| 4,426,251 A | 1/1984 | Ida et al. | |
| 4,426,451 A * | 1/1984 | Columbus | 436/518 |
| 4,446,232 A | 1/1984 | Liotta | |
| 4,431,004 A | 2/1984 | Bessman et al. | |
| 4,431,507 A | 2/1984 | Nankai et al. | |
| 4,434,236 A | 2/1984 | Freytag | |
| 4,468,469 A | 8/1984 | Atkinson et al. | |
| 4,508,613 A | 4/1985 | Busta et al. | |
| 4,508,821 A | 4/1985 | Mansour et al. | |
| 4,517,287 A | 5/1985 | Scheibe et al. | |
| 4,517,291 A | 5/1985 | Seago | |
| 4,533,440 A | 8/1985 | Kim | |
| 4,545,382 A | 10/1985 | Higgins et al. | |
| 4,552,840 A | 11/1985 | Riffer | |
| 4,604,264 A | 8/1986 | Rothe et al. | |
| 4,637,978 A | 1/1987 | Dappen | |
| 4,654,197 A | 3/1987 | Lilja et al. | |
| 4,696,748 A | 9/1987 | Nitadori et al. | |
| 4,708,929 A | 11/1987 | Henderson | |
| 4,711,245 A | 12/1987 | Higgins et al. | |
| 4,790,979 A | 12/1988 | Terminiello et al. | |
| 4,797,256 A | 1/1989 | Watlington, IV | |
| 4,803,170 A * | 2/1989 | Stanton | G01N 33/533 422/412 |
| 4,820,489 A | 4/1989 | Rothe et al. | |
| 4,849,340 A | 7/1989 | Oberhardt | |
| 4,859,583 A | 8/1989 | Heller et al. | |
| 4,871,258 A | 10/1989 | Herpichboehm et al. | |
| 4,883,764 A | 11/1989 | Kloepfer | |
| 4,897,173 A | 1/1990 | Nankai et al. | |
| 4,900,424 A | 2/1990 | Birth et al. | |
| 4,919,770 A | 4/1990 | Preidel et al. | |
| 4,943,522 A | 7/1990 | Eisinger et al. | |
| 4,943,533 A | 7/1990 | Mendelsohn et al. | |
| 4,960,415 A | 10/1990 | Reinmuller | |
| 4,963,815 A | 10/1990 | Hafeman | |
| 4,988,429 A | 1/1991 | Mattheiessen et al. | |
| 4,994,238 A | 2/1991 | Daffern et al. | |
| 5,059,908 A | 10/1991 | Mina | |
| 5,096,809 A | 3/1992 | Chen et al. | |
| 5,120,420 A | 6/1992 | Nankai et al. | |
| 5,122,244 A | 6/1992 | Hoenes et al. | |
| 5,126,034 A | 6/1992 | Carter et al. | |
| 5,128,015 A | 7/1992 | Szuminsky et al. | |
| 5,141,868 A | 8/1992 | Shanks et al. | |
| 5,156,972 A | 10/1992 | Issachar et al. | |
| 5,179,005 A | 1/1993 | Phillips et al. | |
| 5,183,740 A | 2/1993 | Ligler et al. | |
| 5,185,256 A | 2/1993 | Nankai et al. | |
| 5,192,415 A | 3/1993 | Yoshioka et al. | |
| 5,229,282 A | 7/1993 | Yoshioka et al. | |
| 5,268,890 A | 12/1993 | Colescott | |
| 5,272,087 A | 12/1993 | El Murr et al. | |
| 5,272,258 A | 12/1993 | Siegel et al. | |
| 5,306,623 A | 4/1994 | Kiser et al. | |
| 5,312,590 A | 5/1994 | Gunasingham et al. | |
| 5,314,605 A | 5/1994 | Matthiessen et al. | |
| 5,320,732 A | 6/1994 | Nankai et al. | |
| 5,382,346 A | 1/1995 | Uenoyama et al. | |
| 5,384,028 A | 1/1995 | Ito et al. | |
| 5,385,846 A | 1/1995 | Kuhn et al. | |
| 5,393,399 A | 2/1995 | Van den Berg et al. | |
| 5,413,690 A | 5/1995 | Kost et al. | |
| 5,418,142 A | 5/1995 | Kiser et al. | |
| 5,427,912 A | 6/1995 | Brown et al. | |
| 5,434,055 A | 7/1995 | Jernigan | |
| 5,437,999 A | 8/1995 | Diebold et al. | |
| 5,460,924 A | 10/1995 | Buchanan et al. | |
| 5,508,171 A | 4/1996 | Walling et al. | |
| 5,509,410 A | 4/1996 | Hill et al. | |
| 5,518,590 A | 5/1996 | Fang | |
| 5,567,302 A | 10/1996 | Song et al. | |
| 5,602,040 A | 2/1997 | May et al. | |
| 5,628,890 A | 5/1997 | Carter et al. | |
| 5,645,709 A | 7/1997 | Birch et al. | |
| 5,707,584 A | 1/1998 | Terpestra et al. | |
| 5,776,324 A | 7/1998 | Usala | |
| 5,842,787 A | 12/1998 | Kopf-Sill et al. | |
| 5,849,247 A | 12/1998 | Uzan et al. | |
| 5,863,400 A | 1/1999 | Drummond et al. | |
| 5,922,615 A | 7/1999 | Nowakowski et al. | |
| 5,932,711 A | 8/1999 | Boles et al. | |
| 5,942,102 A | 8/1999 | Hodges et al. | |
| 5,951,492 A | 9/1999 | Douglas et al. | |
| 5,965,456 A | 10/1999 | Malmqvist | |
| 5,980,709 A | 11/1999 | Hodges et al. | |
| 5,997,617 A | 12/1999 | Czabala et al. | |
| 5,997,817 A | 12/1999 | Crismore et al. | |
| 6,054,039 A | 4/2000 | Shieh | |
| 6,103,033 A | 8/2000 | Say et al. | |
| 6,193,865 B1 | 2/2001 | Hodges et al. | |
| 6,214,205 B1 | 4/2001 | Willner et al. | |
| 6,218,134 B1 | 4/2001 | Yamauchi et al. | |
| 6,245,296 B1 | 6/2001 | Ligler et al. | |
| 6,325,973 B1 | 12/2001 | Leland et al. | |
| 6,362,328 B1 * | 3/2002 | Fisher et al. | 536/24.3 |
| 6,444,115 B1 | 9/2002 | Hodges et al. | |
| 6,495,823 B1 | 12/2002 | Miller et al. | |
| 6,548,311 B1 * | 4/2003 | Knoll | 436/524 |
| 6,602,702 B1 | 8/2003 | McDevitt et al. | |
| 6,615,856 B2 | 9/2003 | McNeely et al. | |
| 6,632,349 B1 | 10/2003 | Hodges et al. | |
| 6,638,415 B1 | 10/2003 | Hodges et al. | |
| 6,649,403 B1 | 11/2003 | McDevitt et al. | |
| 6,713,545 B2 | 3/2004 | Petiniot et al. | |
| 6,823,750 B2 | 11/2004 | Hodges et al. | |
| 2002/0012943 A1 | 1/2002 | Fowlkes et al. | |
| 2003/0148169 A1 * | 8/2003 | Willner et al. | 429/43 |
| 2003/0180814 A1 | 9/2003 | Hodges et al. | |
| 2004/0203137 A1 | 10/2004 | Hodges et al. | |
| 2007/0250976 A1 | 11/2007 | Beliveau | |

FOREIGN PATENT DOCUMENTS

| | | |
|---|---|---|
| DE | 3708031 | 12/1987 |
| EP | 0 178 647 | 4/1986 |
| EP | 0 251 915 | 1/1988 |
| EP | 0 255 291 | 2/1988 |
| EP | 0 278 647 | 8/1988 |
| EP | 0 280 211 | 8/1988 |
| EP | 0 345 781 | 12/1989 |
| EP | 0 351 516 | 1/1990 |
| EP | 0 400 918 | 12/1990 |
| EP | 0 407 800 | 1/1991 |
| EP | 0 415 679 | 3/1991 |
| EP | 0 422 708 | 4/1991 |
| EP | 0 475 692 | 3/1992 |
| EP | 0 479 394 | 4/1992 |
| EP | 0 560 336 | 9/1993 |
| EP | 0 574 134 | 12/1993 |
| EP | 0 603 954 | 6/1994 |
| EP | 0 640 832 | 3/1995 |
| EP | 0 741 186 | 11/1996 |
| EP | 0 764 469 | 3/1997 |
| EP | 0 796 659 | 9/1997 |
| EP | 0 803 288 | 10/1997 |
| EP | 0 964 059 | 12/1999 |
| EP | 1 347 302 | 9/2003 |
| FR | 2667943 | 4/1992 |
| GB | 2201248 | 8/1988 |
| JP | 8136496 | 5/1996 |
| JP | 95/02799 | 3/1997 |
| JP | 10221341 | 2/1998 |

(56) References Cited

FOREIGN PATENT DOCUMENTS

| | | |
|---|---|---|
| JP | 2001/059845 | 3/2001 |
| JP | 2001-153838 | 6/2001 |
| JP | 2002-536660 | 10/2002 |
| TW | 373073 | 11/1999 |
| TW | 406188 | 9/2000 |
| WO | WO 89/08713 | 9/1989 |
| WO | WO 92/15701 | 9/1992 |
| WO | WO 94/03496 | 2/1994 |
| WO | WO 95/16198 | 6/1995 |
| WO | WO 95/21934 | 8/1995 |
| WO | WO 95/28634 | 10/1995 |
| WO | WO 97/00441 | 1/1997 |
| WO | WO 97/18464 | 5/1997 |
| WO | WO 97/27474 | 7/1997 |
| WO | WO 98/11426 | 3/1998 |
| WO | WO 98/18465 | 5/1998 |
| WO | WO 98/43074 | 10/1998 |
| WO | WO 99/46585 | 9/1999 |
| WO | WO 99/49307 | 9/1999 |
| WO | WO 2000/047983 | 8/2000 |
| WO | WO 02/08763 | 1/2002 |
| WO | WO 98/43073 | 6/2003 |
| WO | WO 05/26178 | 3/2005 |
| WO | WO 05/26689 | 3/2005 |

OTHER PUBLICATIONS

Chinese Intellectual Property Office, Second Office Action in corresponding Chinese Patent Application No. 200610149310.5, dated Jan. 21, 2012, 3 pages.
European Patent Office, European Search Report in corresponding European Patent Application No. EP 03251762, dated Nov. 5, 2003, 7 pages.
European Patent Office, Examination Report in corresponding application No. EP 0196164.6, dated Nov. 7, 2008, 5 pages.
European Patent Office, European Search Report & Written Opinion in corresponding European Patent Application No. EP 06255939.8, dated Feb. 27, 2007, 6 pages.
European Patent Office, Summons to Attend Oral Proceedings in corresponding European Patent Application No. EP 06255939.8, dated Apr. 15, 2009, 8 pages.
European Patent Office, Decision to Grant in corresponding European Patent Application No. EP 06255939.8, dated Apr. 14, 2011, 2 pages.
Gibilisco, S; *Electrode*; McGraw-Hill Prof, 8d, 2001, p. 237.
Gribnau, CJ et al; Particle-labelled immunoassays: a review; Journal of Chromatography, Biomedical Applications 1986; 376, pp. 175-189.
Japanese Patent Office, Official Action in corresponding application No. JP 2003/078391, dated Sep. 25, 2007, 2 pages.
Japanese Patent Office, Official Action in corresponding application No. JP 2003/078391, dated Aug. 5, 2008, 3 pages.
Japanese Patent Office, Notice of Reasons for Rejection in corresponding application No. JP 2006/213451, dated Sep. 13, 2011, 3 pages.
Kresl et al; "Conversion of native oligometric to a modified monomeric form of human C-reactive protein;" *The Internati onal Journal of Biochemistry and Cell Biology* 1998, 30, pp. 1415-1426.
Minton, 1981, Biopolymers, 20, pp. 2093-2120.
Miyahara, Abstract in Japanese patent application No. JP 6310746, Nov. 4, 1994.
Patent Cooperation Treaty, International Search Report in corresponding application No. PCT/FR94/01023, dated Nov. 23, 1994, 4 pages.
Patent Cooperation Treaty, International Search Report in corresponding application No. PCT/US01/22202, dated Apr. 15, 2002, 3 pages.
Ronkainen-Matsuno, NJ, et al., "Electrochemic Allmmonoassay Moving into the Fast Lane," *Trends in Analytical Chemistry*, vol. 21, No. 4, 2002, pp. 213-225.
Tsar & Tsai, Correspondence from foreign associate regarding English Translation of TIPO's Search Report, e-mailed on Jul. 11, 2008, 4 pages.
USPTO, Non-Final Office Action in corresponding U.S. Appl. No. 11/284,097, dated Mar. 27, 2008, 6 pages.
USPTO, Non-Final Office Action in corresponding U.S. Appl. No. 11/284,097, dated Jun. 18, 2009, 12 pages.
European Patent Office, European Extended Search Report in corresponding European Patent Application No. EP 10179412, dated Sep. 9, 2011, 10 pages.
Japanese Patent Office, Decision of Rejection in corresponding Application No. JP 2006-312451, dated May 15, 2012, 2 pages.
Chinese Patent Office, Decision of Rejection in corresponding Application No. CN 2006-10149310.5, dated Oct. 29, 2012, 15 pages.
Coligan, *Short Protocols in Immunology: A Compendium of Methods from Current Protocols Immunology*, 2005, pp. 4-6, John Wiley & Sons, Inc., Hoboken, NJ.
European Patent Office, Summons mailed in counterpart European Patent Application No. 10179412.1, dated Apr. 28, 2014, 4 pgs. (received May 9, 2014).
O'Sullivan et al., "Comparison of two methods of preparing enzyme-antibody conjugates: application of these conjugates for enzyme immunoassay," Anal. Biochem., Nov. 15, 1979, pp. 100-108, vol. 100(1).

\* cited by examiner

BIOSENSOR APPARATUS AND METHODS OF USE

RELATED APPLICATIONS

This application claims priority as a divisional application to U.S. application Ser. No. 11/284,097, filed Nov. 21, 2005, entitled "Biosensor Apparatus and Methods of Use," now abandoned, which in turn claims priority as a continuation-in-part to U.S. application Ser. No. 10/105,050, entitled "Direct Immunosensor Assay," filed Mar. 21, 2002, and Ser. No. 10/830,841, entitled "Immunosensor," filed Apr. 22, 2004, all of which are hereby incorporated by reference in their entirety.

BACKGROUND OF THE INVENTION

Conventional biomedical sensors, including immunoassays based systems, have been used to report the presence and/or concentration of a wide variety of analytes. Immunoassays are generally classified into two categories: competition assays and sandwich assays. In a competition assay, the antigen in the test sample is mixed with an antigen-probe complex (commonly referred to as a reporter complex) and the mixture then competes for binding to the antibody. The probe may be a radioisotope, a fluorophore, or a chromophore. In a sandwich immunoassay, the antigen in the test sample binds to the antibody and then a second antibody-probe complex binds to the antigen. In these prior art assay methods, one or more washing steps are usually required. The washing steps introduce complexity into the assay procedure and can generate biohazardous liquid waste.

Immunoassays usually provide a user with either a qualitative result (e.g., a "yes/no answer") obtained, most often by a simple visual detection (e.g., color change), or a quantitative result such as a concentration of an antigen. Most of the quantitative methods involve expensive pieces of equipment, such as scintillation counters (for monitoring radioactivity), spectrophotometers, spectrofluorimeters (see, e.g., U.S. Pat. No. 5,156,972), surface plasmon resonance instruments (see, e.g., U.S. Pat. No. 5,965,456), and the like. It would therefore be advantageous to develop an immunoassay that is both inexpensive and simple enough to use to be suitable for home or field use. Such an biosensor would preferably require no centrifugation, dilution, pipetting, washing, or timing steps, and would generate minimal waste.

SUMMARY OF THE INVENTION

Disclosed herein are biosensor devices and methods for detecting and/or quantifying an analyte of interest. In one embodiment, a disposable assay device is provided for use in detecting a target analyte in a fluid sample, the device including a reaction chamber with an immobilized binding target and a probe conjugate positioned therein. When a sample is introduced into the reaction chamber a binding reaction occurs between the immobilized binding target, probe conjugate, and/or target analyte (if present). In one exemplary embodiment, if the target analyte is present, it causes a change in the amount of probe conjugate that is bound to the immobilized binding site. This change can be detected in a detection chamber.

The immobilized binding target, probe conjugate, and target analyte can include the variety of known ligands. For example, one skilled in the art will appreciate that the immobilized binding target, probe conjugate, and target analyte can include an antigen or antibody, a hormone or neurotransmitter and a receptor, a substrate or allosteric effector and an enzyme, lectins and sugars, DNA or RNA structures, such as aptamers and their binding species (including other DNA or RNA species or binding protein), proteins, biotin and adivin or streptavidin systems, enzymes and their substrates and inhibitors, lipid binding systems, and combinations thereof. To facilitate understanding of the devices and methods described herein, immunological ligands will be described henceforth and the device will be referred to as an immunosensor or a biosensor.

In one aspect, the detection chamber mentioned above includes electrodes and electrochemical reagents. For example, an electrochemical reaction in the detection chamber can be used to determine if the amount of probe conjugate bound in the reaction chamber has been increased or reduced by the presence of the target antigen. The electrochemical reaction can also be used to determine the analyte (e.g., target antigen) concentration based on the concentration of the probe conjugate in the detection chamber.

In one embodiment, the immobilized binding site includes an antibody adapted to bind to a target antigen and the probe conjugate includes an antibody adapted to bind to a bound target antigen. If a target antigen is present in a fluid sample, the immobilized binding site can bind to one site on the target antigen, and the probe conjugate can bind to another site on the target antigen. The presence of a target antigen in the fluid sample thus results in an increase in the amount of probe bound in the reaction chamber and a reduction in the amount of probe conjugate in the detection chamber.

In another embodiment, the immobilized binding site includes a target antigen and the probe conjugate includes an antibody adapted to bind to the target antigen. When a sample is introduced into the reaction chamber, a target antigen, if present, will bind with the probe conjugate. As a result, the presence of a target antigen in the fluid sample results in a reduction in the amount of probe conjugate bound to the immobilized binding site in the reaction chamber and an increase in the amount of unbound probe conjugate that can travel to a detection chamber. The reduction in bound probe conjugate can be detected and/or quantified by an electrochemical reaction in the detection chamber. Conversely, the immobilized binding site can include an antibody and the probe conjugate can include the target antigen. The presence of target antigen in the fluid sample will similarly cause a reduction in the amount of bound probe conjugate in the reaction chamber.

In one aspect, the immobilized binding sites and the probe conjugate are intermixed in the reaction chamber. Alternatively, the immobilized binding sites and the probe conjugate are positioned separately. For example, immobilized binding sites can be located on magnetic beads that are dried on a surface of the reaction chamber. When a liquid sample is introduced into the reaction chamber, a magnetic field can be used to keep the magnetic beads and immobilized binding sites from moving into the detection chamber.

In another embodiment disclosed herein, a method of detecting a target antigen in a fluid sample is provided. The method can include the steps of delivering a sample to an biosensor device that includes a reaction chamber and a detection chamber. The sample is allowed to react with immobilized binding sites and a probe conjugate positioned within the reaction chamber. The sample is then moved to a detection chamber, and the method further comprises the step of electrochemically detecting the probe conjugate in the detection chamber. The detection step allows a user to determine if the target antigen is present in the sample based on the level of probe conjugate detected in the detection chamber. The method can also include the step of quantifying the amount of target antigen in the sample based on electrical signals received from the detection chamber.

BRIEF DESCRIPTION OF THE DRAWINGS

The invention will be more fully understood from the following detailed description taken in conjunction with the accompanying drawings, in which.

DETAILED DESCRIPTION OF THE INVENTION

Described herein are biosensor devices and methods of use. In one embodiment, the sensor includes a reaction chamber and a detection chamber. Positioned within the reaction chamber are immobilized binding sites that bind to the analyte of interest or to species related to the analyte of interest. Also in this chamber is a probe species that can be detected in the detection chamber, and which can be conjugated to a species that can bind to the immobilized binding site, or which can bind to a species that binds to the immobilized binding site. This will be hereafter termed the probe conjugate. The probe conjugate and the immobilized binding site are such that the presence of the analyte of interest in the sample modifies the interaction of the probe conjugate and the immobilized binding site. For example, when present, the analyte can block the probe conjugate from binding to the immobilized binding site. Alternatively, the analyte can provide a site for the probe conjugate to bind, thereby increasing the amount of bound probe conjugate. In either embodiment, the presence of analyte modifies the amount of the probe conjugate bound in the reaction chamber.

The reaction chamber can be arranged so that after the probe conjugate binding reactions have taken place to the desired extent, the liquid from the reaction chamber is transferred to the detection chamber, transferring with it the free probe conjugate and leaving behind the bound probe conjugate. In the detection chamber, the amount of free probe conjugate can be detected. For example, electrodes in the detection chamber can be used to electrochemically detect the level of probe conjugate in the detection chamber. The electrochemical reaction can determine if the target analyte is present/absent and/or determine the concentration of the target analyte based on the amount of the probe conjugate in the detection chamber.

Figure 1:
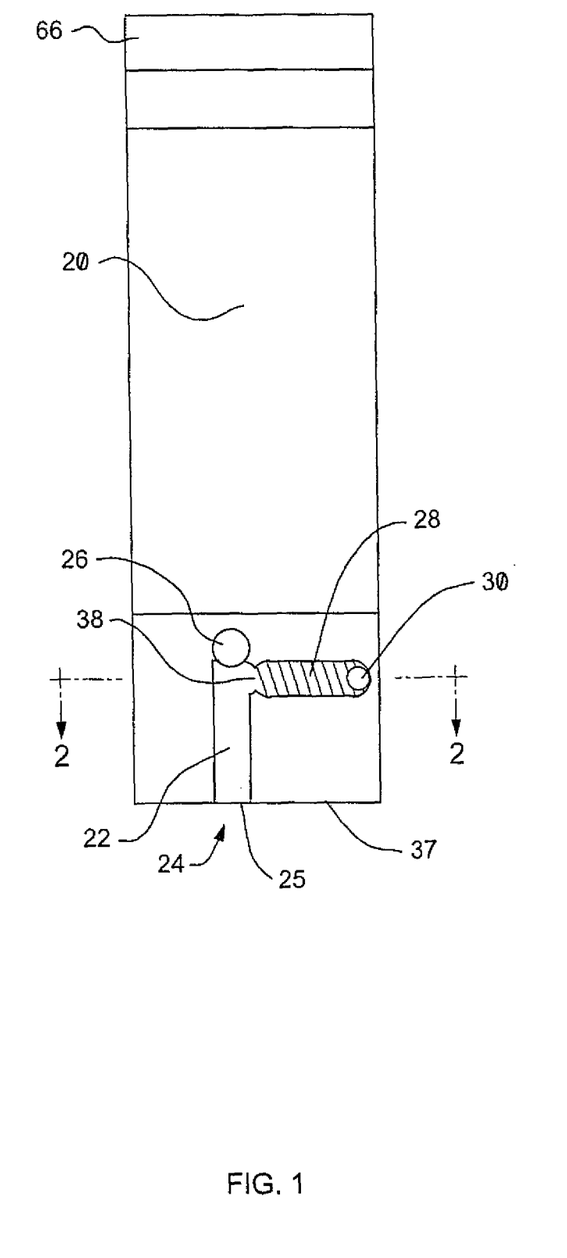
FIG. 1 is a top view of one embodiment of an biosensor disclosed herein.
Figure 2:
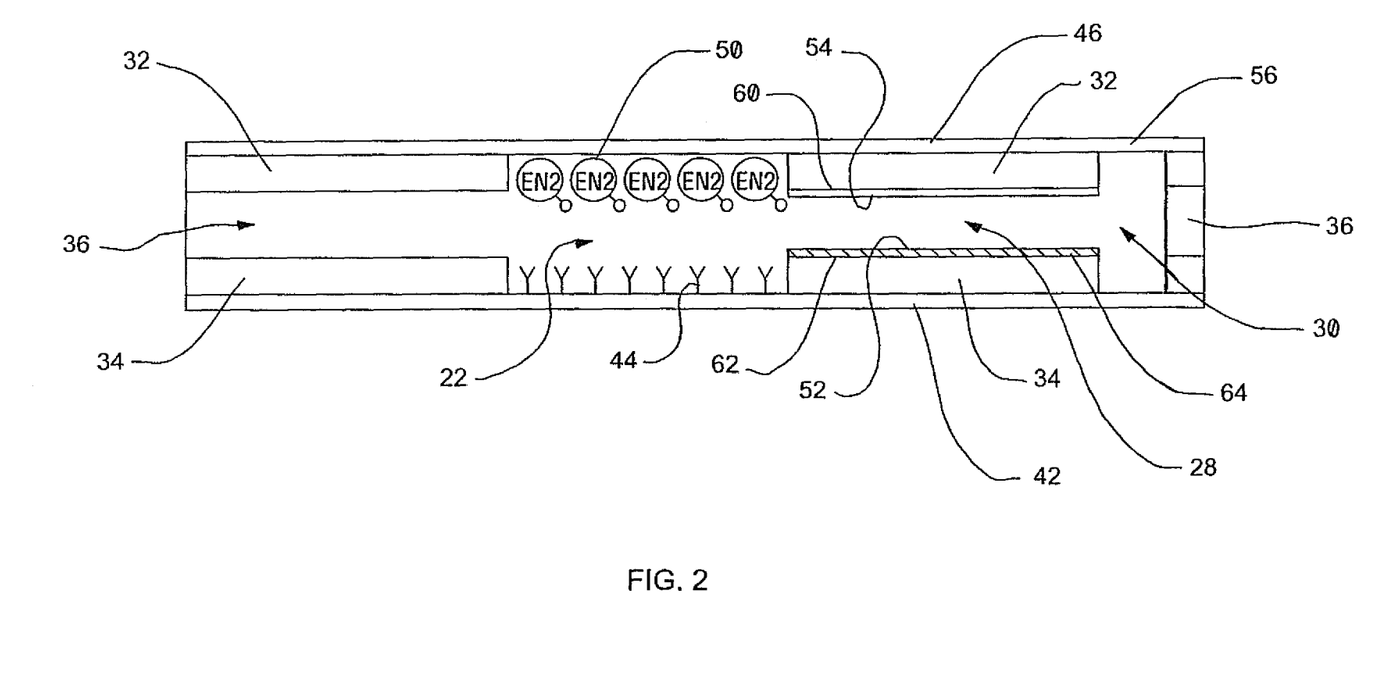
FIG. 2 is a cross-sectional view of the biosensor of FIG. 1 along line A-A'.

A first embodiment of a biosensor 20, illustrated in FIGS. 1 and 2, includes a detection chamber 28 comprising an electrochemical cell and a reaction chamber 22 containing immobilized binding sites and a probe conjugate. The detection chamber 28 and reaction chamber 22 can be prepared by forming an aperture extending through a sheet of electrically resistive spacer material 36. The aperture can be shaped such that it defines a sidewall of both the reaction chamber 22 and detection chamber 28, as well as a sample passageway 38 between chambers 22, 28. By extending the aperture from a proximal end 24 of reaction chamber 22 through to an edge 37 of sensor 20, a sample ingress 25 is also formed. In one embodiment, the thickness of sheet 36 defines the height of the reaction chamber 22 and detection chamber 28, and the chambers can have an equal height. According to this embodiment the capillary force in the detection chamber must be greater than that in the reaction chamber. This can be achieved by modifying the surfaces of the reaction chamber and/or detection chamber or by adding filling materials, such as those herein disclosed, to the detection chamber.

In another embodiment, the height of reaction chamber 22 is greater than that of detection chamber 28. A reaction chamber 22 of greater height than detection chamber 28 can be prepared, for example, by layering multiple inner sheets 32, 34, 36 and/or outer sealing sheets 42, 46 together. For example, in FIG. 2 the middle sheet 36 of sensor 20 has an aperture defining the sidewalls of reaction chamber 22 and detection chamber 28 as described above. Middle sheet 36 is then sandwiched between one or more additional layers 32, 34, the additional layers 32 and 34 having an aperture corresponding only to reaction chamber 22. With respect to detection chamber 28, layers 32 and 34 define the end walls 60, 62 (i.e., top and bottom surfaces) of the chamber. In this embodiment, the end walls 60 and 62 of the detection chamber comprise electrodes 54 and 52, electrically connectable, via connection means, to a measuring circuit. The electrodes are described in more detail below.

In one aspect, the electrodes 52 and 54 can be placed in electrical connection with a meter (not shown) through the connection end 66. The connection end allows a meter (not shown) to electrically communicate with the electrodes 52 and 54 in the detection chamber 28 via electrically conductive tracks (not shown). The meter in connection with the connection area 66 is capable of applying a potential between the electrodes 52 and 54 in the detection chamber 28 and detecting the electrical signals generated during an electrochemical reaction.

In use, a user first introduces sample into the first chamber, the reaction chamber 22, of the sensor through sample ingress 25. The sample can be drawn into the reaction chamber under the influence of capillary or wicking action. The reaction chamber can include a vent 26 that is open to the atmosphere, thus allowing air displaced by the sample to escape. Sample will be drawn into the first chamber until it is filled up to the reaction chamber vent 26, whereupon filling will stop. The volume of reaction chamber 22 is chosen so as to be at least equal to and preferably larger than the volume of the detection chamber 28.

The dashed circle in FIG. 1 denotes an aperture 30 piercing layers 32, 34, and/or 36 but not layers 42 and 46. Since layers 42 and 46 are not pierced initially, the only opening to the atmosphere of the detection chamber 28 is through sample passageway 38 that opens from reaction chamber 22. Thus, when reaction chamber 22 fills with sample, air is trapped in detection chamber 28, which substantially prevents it from filling with sample. A small amount of sample can enter the detection chamber 28 during the time between when the sample first contacts the opening 38 to the detection chamber 28 and when it contacts the far side of the opening 38. However, once the sample has wet totally across the opening 38 to the detection chamber 28, no more filling of detection chamber 28 will take place.

The opening of a vent 56 to the atmosphere allows the air trapped in the detection chamber 28 to escape, thereby permitting detection chamber 28 to be filled with reacted sample from reaction chamber 22. Vent 56 can be opened in a variety of ways, including, for example, by puncturing an outer layer of the device, by removing a portion of the outer layer of the device, and/or by tearing away a portion of the device.

When the vent is opened, the reacted sample will be drawn into the detection chamber 28 due to increased capillary force in the detection chamber 28 compared to that present in the reaction chamber 22. In one embodiment, the increased capillary force is provided by suitably coating the surfaces of the detection chamber 28 or, more preferably, by choosing the capillary distance for detection chamber 28 to be smaller than that of reaction chamber 22. In this embodiment, the capillary distance is defined to be the smallest dimension of the chamber. One skilled in the art will appreciate that the capillary forces in the reaction and/or detection chambers can be created by varying a number of factors. Capillary forces in thin chambers are discussed, for example, in U.S. Pat. No. 6,823,750, entitled "Method of Preventing of Preventing Short Sampling of a Capillary or Wicking Fill Device," which is hereby incorporated by reference in its entirety.

Figure 3:
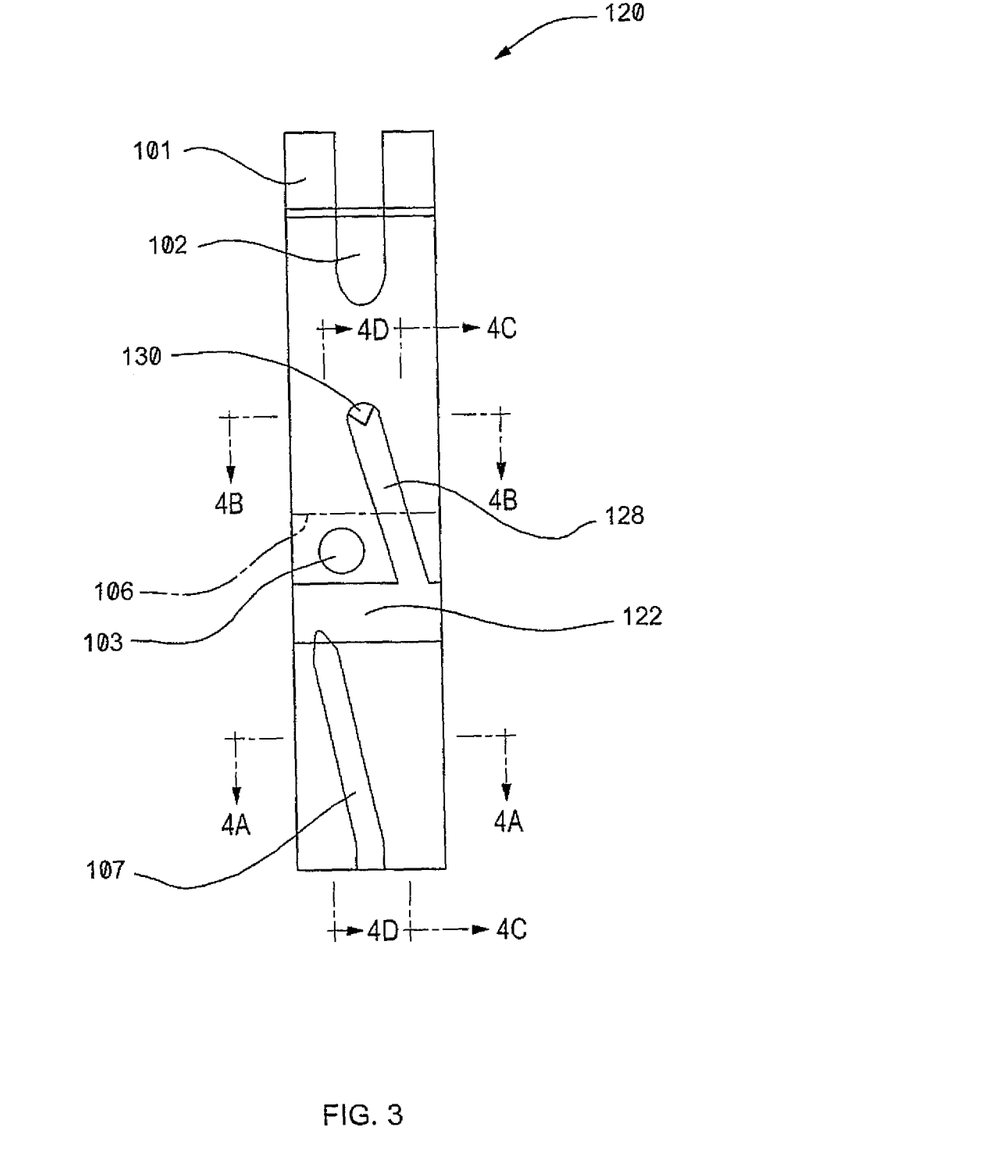
FIG. 3 is a top view of another embodiment of a biosensor disclosed herein.
Figure 4A:
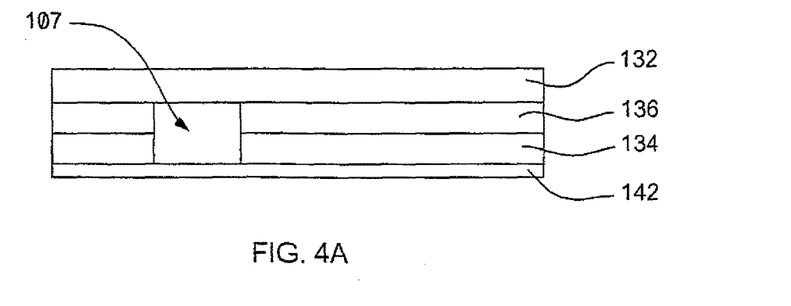
FIG. 4A is a cross-sectional view of the biosensor of FIG. 3 along the line A-A'.
Figure 4B:
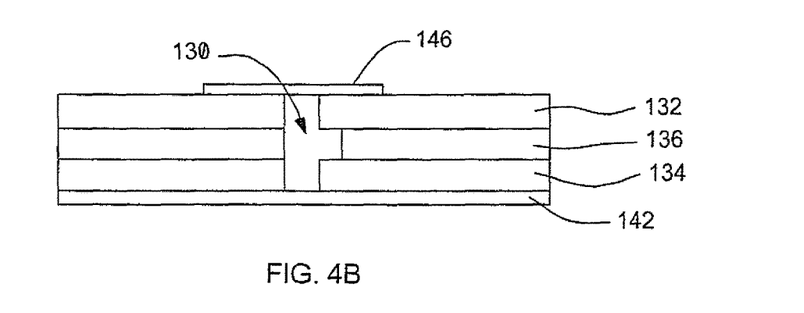
FIG. 4B is a cross-sectional view of the biosensor of FIG. 3 along the line B-B'.
Figure 4C:
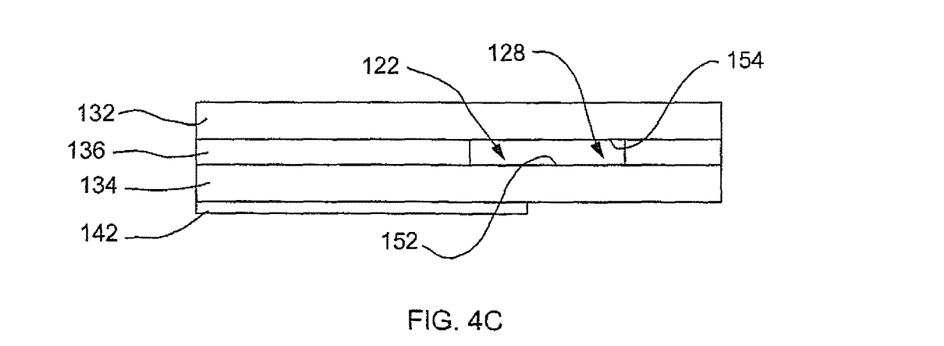
FIG. 4C is a cross-sectional view of the biosensor of FIG. 3 along the line C-C'.
Figure 4D:
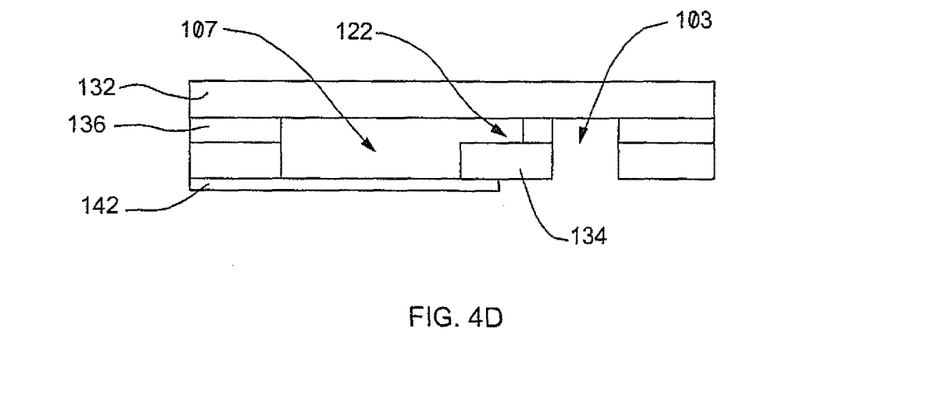
FIG. 4D is a cross-sectional view of the biosensor of FIG. 3 along the line D-D'.

A second exemplary embodiment of a biosensor 120, including three chambers, is illustrated in FIGS. 3 through 4D. The immunosensor can include a filling chamber 107 in addition to a reaction chamber 122 and a detection chamber 128. Sensor 120 can be formed from multiple layers as described above, including for example, a sealing layer 142, a lower layer 134, a spacer layer 136, and an upper layer 132. In one aspect, each layer comprises an insulating material, while upper and lower layers 132, 134 additionally include an electrically conductive film as discussed in more detail below. By removing portions of the layers at different points in the sensor, a filing chamber 107, reaction chamber 122, and a detection chamber 128 are formed. In addition, exposing portions of the electrically conductive film on the upper and lower layers 132, 134 provides electrodes 152, 154 for performing electrochemical reactions and provides electrical contact areas 101, 102, 103 for electrically connecting the sensor to a meter.

Filling chamber 107 receives the sample from the patient or user and provides a reservoir of sample for filling the other two chambers. Reaction chamber 122 and detection chamber 128 are in fluid communication with filling chamber 107. To assist with moving fluid between chambers, detection chamber 128 can include vent 130 which is initially closed. After a sample is reacted in the reaction chamber, vent 130 is opened so that air in detection chamber 128 can exit through the vent allowing liquid from reaction chamber 122 to enter the detection chamber. As discussed above with respect to vent 56, vent 130 can be opened in a variety of ways, including piercing the device, removing an outer layer, and/or tearing a portion of the device (i.e., tearing along a perforation).

The sensor can include electrical connection point 101 that allows an electrical connection to be made to a lower electrode 152 and electrical connection points 102, 103 that allow an electrical connection to an upper electrode 154. Dotted line 106 denotes a break in the electrically conductive film defining upper electrode 154 on upper layer 132. The break may be affected by patterning the conductive film when it is laid down or by creating the break during manufacture. The break could be affected by scratching the film, scraping part of the film away, chemically etching the film, laser ablating the film or other methods as commonly known. Break 106 in the conductive film serves to, in part, define the active electrode area of the strip by electrically isolating the conductive coated in the detection chamber from that in the reaction chamber. This is advantageous as it can prevent any electric signal that might otherwise flow at the conductive films in the reaction chamber from effecting the test results.

Sensor 120 can also include contact point 103 which allows a user to electrically connect to the portion of conductive film in contact with reaction chamber 122. As reaction chamber 122 fills with sample, monitoring contact point 103 allows a signal to be detected that indicates to the meter that the strip has been successfully filled and a test sequence can commence. In order to accomplish this with the embodiment of the invention shown in FIGS. 3 through 4D, an electrical connection could be made to the lower conductive film at contact point 101 and to the upper conductive film in the reaction chamber at contact point 103. A potential would then be applied between the two connection points (101, 103) and the current, voltage, and/or electrical resistance monitored to ascertain when sample has entered the reaction chamber. This potential may be a DC potential or it may be a potential that varies with time such as an AC potential or a series of square wave potential pulses with alternating polarity. By monitoring the current that flows as a result of the potential application, or the voltage required to pass a pre-determined current, an indication of when the conductive films in the reaction chamber begin to wet can be obtained.

Connection area 101, for electrically contacting a lower layer 134 carrying the lower conductive film, can be formed by extending lower layer 134 out past the end of a spacer layer 136 and the upper layer 132. Contact area 102 is formed by removing sections of layers 134 and 136 to expose a section of upper layer 132. Contact area 103 is similarly formed by removing a section of lower layer 134 and spacer layer 136 as shown in FIG. 4D (cross-section D-D' In FIG. 3).

Filling chamber 107 can be formed by removing sections of lower layer 134 and spacer layer 136, but leaving upper layer 132 and sealing layer 142 intact. Sealing layer 142 can be adhered to the outside face of layer 134 and can serve, with the sides of the cut-out sections in layers 134 and 136 and layer 132, to form a capillary channel which is capable of drawing sample into it by capillary action. This channel is illustrated in FIG. 4A (cross-section A-A' in FIG. 3).

Reaction chamber 122 is formed by removing a section of the spacer layer 136 but leaving layers 134 and 132 intact. This forms a capillary space where the height of the capillary spacer is smaller than the height of the filling chamber 122. This allows capillary forces to draw liquid from the filling chamber 122 into the reaction chamber 128 by capillary action. The small height of the reaction chamber can also allow for relatively rapid mixing of components in the reaction chamber. In one aspect, reaction chamber 122 opens at the lateral edge(s) of the strip to allow air to vent while liquid fills the reaction chamber.

Detection chamber 128 is formed in a similar fashion to the reaction chamber 122 by removing a section of the spacer layer 136 while leaving the layers 134 and 132 intact. Initially, the detection chamber 128 opens to the reaction chamber 122 at one end but has no other opening.

Vent hole 130 is incorporated into the detection chamber 128 by removing sections of or piercing upper layer 132 (or lower layer 134). A layer 146 shown in FIG. 4B (cross-section B-B' in FIG. 3) can be laminated to the upper face of the strip to seal off the opening. Alternatively, if a portion of lower layer 134 is removed, sealing layer 142 can be pierced/removed to open vent hole 130.

When liquid sample fills reaction chamber 122, as part of the filling process it will bridge the opening of detection chamber 128. Thus, when liquid fills reaction chamber 122 such that it runs across the opening of detection chamber 128, air is trapped in detection chamber 128 preventing further liquid from entering. This allows liquid to be held in reaction chamber 122 while the binding reactions are proceeding. After a predetermined time when any binding reactions that might be occurring in reaction chamber 122 have proceeded to the desired extent, layers 142 or 146 are pierced by a piercing means (or removed/torn away) to allow air to escape detection chamber 128, such that liquid transfers from reaction chamber 122 to detection chamber 128. The cross-sectional dimension of detection chamber 128 allow capillary action to fill the detection chamber.

One skilled in the art will appreciate that the immunosensor described herein can have a variety of alternative configurations such as, for example, the shape of the sensor, the number of chambers, the electrode configuration, and/or the placement of electrical contact points. For example, other sensor devices that are illustrative of a variety of alternative sensor embodiments are disclosed in a U.S. Application entitled "Method and Apparatus for Electrochemical Analysis," filed concurrently herewith and incorporated by reference in its entirety. In addition, one skilled in the art will appreciate that while the illustrated sensors use vents to control the flow of fluid between chambers, other fluid directing embodiments are also contemplated. For example, a physical barrier between the reaction chamber and the detection chamber could be removed or opened to permit the flow of fluid between chambers. The sensors described herein could also include pumping elements to move fluids through the device.

The immunosensor of the present invention includes electrodes 52, 152 and 54, 154 as described above. In certain embodiments, an electrode configuration other than the opposing relationship illustrated in the FIGS. may be used, for example, a side-by-side relationship, or an offset relationship. The electrodes may be identical or substantially similar in size, or may be of different sizes and/or different shapes. The electrodes may comprise the same conductive material, or different materials. Other variations in electrode configuration, spacing, and construction or fabrication will be apparent to those of skill in the art.

In one embodiment, the electrodes are mounted in a parallel opposing relationship at a distance of less than or equal to 500, 450, 400, 350, 300, 250, or 200 microns, and more preferably from about 5, 10, 15, 20, 25, 30, 35, 40, 45, or 50 microns to about 75, 100, 125, 150, or 175 microns. In certain embodiments, however, it may be preferred that the electrode spacing is greater than 500 microns, for example, 600, 700, 800, 900, or 1000 microns, or even greater than 1, 2, 3, 4, or 5 millimeters.

At least one of the electrodes can be a sensing electrode, i.e., an electrode sensitive to the amount of reduced redox agent in the antioxidant case or oxidized redox agent in the oxidant case. In the case of a potentiometric sensor wherein the potential of the sensing electrode is indicative of the level of analyte present, a second electrode, acting as reference electrode is present which acts to provide a reference potential. In the case of an amperometric sensor wherein the sensing electrode current is indicative of the level of analyte in the sample, at least one other electrode is present which functions as a counter electrode to complete the electrical circuit. This second electrode may also function as a reference electrode. Alternatively, an additional electrode (not shown) may perform the function of a reference electrode.

In one aspect, the electrically conductive film defining electrodes 52, 152, 54, 154 can be adhered to a surface the immunosensor by means of an adhesive. Suitable adhesives include, for example, heat activated adhesives, pressure sensitive adhesives, heat cured adhesives, chemically cured adhesives, hot melt adhesives, hot flow adhesives, and the like. In an alternative aspect, the electrically conductive film is prepared by coating (e.g., by sputter coating or screen printing) a sheet of electrically resistive material with a suitable electrically conductive material, for example, platinum, palladium, carbon, indium oxide; tin oxide, mixed indium/tin oxides, gold, silver, iridium, mixtures thereof, and the like. Materials suitable for use as the electrodes should be compatible with the reagents present in the sensor 20, 120. Suitable electrically resistive materials include, for example, polyesters, polystyrenes, polycarbonates, polyolefins, mixtures thereof, and the like.

Reagents for use in the immunosensor, e.g., immobilized antibody/antigen, probe-linked antigen/antibody, buffer, mediator, enzyme substrate, and the like, may be supported on the walls the reaction chamber 22, 122 or on an independent support contained within chambers, within a matrix, or may be self supporting. If the reagents are to be supported on the chamber walls or the electrodes, the chemicals can be applied by use of printing techniques well known in the art, e.g., ink jet printing, screen printing, lithography, and the like. In an alternative embodiment, a solution containing the reagent is applied to a surface within a chamber and allowed to dry.

In another embodiment of the immunosensor described herein, immunological species and/or electrochemical reagents can be supported on and/or contained within one or more independent supports which are placed into the sensor. Suitable independent supports include, but are not limited to, mesh materials, nonwoven sheet materials, fibrous filling materials, macroporous membranes, sintered powders, and/or beads. The advantages of independent supports include an increased surface area, thus allowing more immobilized binding sites and probe conjugate to be included in the reaction chamber 22, 122. In one embodiment, an immobilized antibody and/or probe conjugate are dried onto support materials, which are then placed into the reaction chamber. Alternatively, either the immobilized binding site or probe conjugate is incorporated onto a support material and the other component is supported on the reaction chamber wall. In yet another embodiment, the walls of the reaction chamber are porous, with the immobilized binding site and/or probe conjugate incorporated therein. This can be accomplished by using a macroporous membrane to form the reaction chamber wall and compressing the membrane around the reaction chamber to prevent leakage of sample out of the desired area.

Suitable independent supports include material such as mesh materials, nonwoven sheet materials, and fibrous fill materials include, polyolefins, polyesters, nylons, cellulose, polystyrenes, polycarbonates, polysulfones, mixtures thereof, and the like. Suitable macroporous membranes may be prepared from polymeric materials including polysulfones, polyvinylidene difluorides, nylons, cellulose acetates, polymethacrylates, polyacrylates, mixtures thereof; and the like.

In one embodiment, the immobilized binding site and/or probe conjugate is supported on beads. Such beads may comprise a polymeric material, e.g., agarose, polystyrene, polymethacrylate, polymethylmethacrylate, optionally encasing a magnetic material (such as gamma $Fe_2O_3$ and $Fe_3O_4$). The bead material is selected such that suitable support for the antibody is provided. Suitable beads may include those marketed as DYNABEADS® by Dynal Biotech of Oslo, Norway. Optionally, a magnet may be included to hold the magnetic beads in the reaction chamber and to stop them from moving to the detection chamber. For example, the immobilized biding site can be positioned on magnetic beads within the reaction chamber.

Using the Sensor to Determine the Presence or Absence of an Antigen

As discussed above, sensor 20, 120 can include an immobilized binding site and a probe conjugate. While the following description is made with respect to sensor 20 of FIG. 2, it will be apparent that it applies to sensor 120 as well.

In one embodiment, an immobilized binding site 44 is an antibody to the antigen to be detected and the probe conjugate 50 is an enzyme linked to the antigen to be detected or a pseudo-antigen of the antigen to be detected.

The antibodies 44 can be adsorbed or otherwise immobilized therein such that they do not move from the reaction chamber during a test. Optionally, after application of the antibodies 44 to the internal surface the reaction chamber, an agent designed to prevent non-specific binding of proteins to this surface can be applied (not shown). An example of such an agent well known in the art is bovine serum albumin (BSA). A nonionic surfactant may also be used as such an agent, e.g., TRITON X100 manufactured by Rohm & Haas of Philadelphia, Pa., or TWEEN manufactured by ICI Americas of Wilmington, Del. Preferably, the nonionic surfactant selected does not denature proteins.

Spaced apart from the antibodies is probe conjugate 50 (enzyme-linked antigen). Examples of suitable enzymes for use with probe conjugate 50 include, but are not limited to, glucose oxidase and glucose dehydrogenase. The enzyme-linked antigen 50 can be deposited within the reaction chamber in such a way that it can be liberated into the sample when wetted by the sample. For example, the enzyme-linked antigen 50 can be dried on a surface within the reaction chamber, such that only a weak bond between the enzyme-linked antigen 50 and the reaction chamber exists. In one aspect, the rate of dissolution of the enzyme-linked antigen 50 is chosen such that probe conjugate will dissolve in a sample during the time taken for the sample to fill the reaction chamber. In this manner, the enzyme-linked antigen 50 can be evenly distributed throughout the area of the reaction chamber after filling.

In one aspect, the relative amounts of enzyme-linked antigen 50 and antibody 44 can be chosen such that there is an excess of antibody 44 over enzyme-linked antigen 50. In one aspect, an excess is defined to be such that the excess is small when compared to the number of antigen molecules to be detected in the sample.

Thus, when sample fills the reaction chamber the enzyme-linked antigen 50 mixes with the sample. Sufficient time is then allowed for the enzyme-linked antigen 50 to come into contact with the antibodies 44. Since there is an excess of antibodies 44, if no antigen is present in the sample then substantially all, or a large portion, of the enzyme-linked antigen 50 will bind to the antibodies 44 and so be effectively immobilized. If target antigen is present in the sample, the target antigen will contact and bind to the antibodies 44, blocking at least some of the enzyme-linked antigen 50 from binding with the antibodies 44. So, when the target antigen is present in the sample, then at the end of the reaction step, the enzyme-linked antigen 50 (or at least a measurable portion thereof) will remain mobile in the sample and can move into the detection chamber. Conversely, if no target antigen is present in the sample, then the enzyme-linked antigen 50 will be immobilized in reaction chamber 22 (or at least a measurable reduction in the amount remaining mobile in the sample). One skilled in the art will appreciate that an excess of antibody 44 is not necessary and that alternatively, the relative amounts of enzyme-linked antigen 50 and antibody 44 can be equal, or an excess of enzyme-linked antigen 50 can be present.

In a second embodiment, the immobilized binding site 44 is an antibody that can bind to a site on the target antigen and the probe conjugate 50 includes an enzyme coupled to an antibody that can bind to bound target antigen. An advantage of using antibodies for the immobilized binding site and for the probe conjugate is that the target binding reagents can be intimately mixed and dried down together during the manufacture of the strip. The distance that the binding targets must diffuse can be shorter, which potentially shortens the time required to perform the assay.

When the sample enters the reaction chamber, the immobilized binding site in the reaction chamber can bind to one site on the analyte of interest. The probe conjugate can include a second antibody that can bind to a second site on the target antigen attached to the immobilized binding site. When a sample containing the analyte of interest fills the reaction chamber, the probe conjugate and the immobilized binding site mix with the sample and the analyte of interest binds at one site to the probe conjugate and at a second site to the immobilized binding site. The analyte therefore forms a link that immobilizes a fraction of the probe conjugate, where the fraction immobilized can be used to detect the presence and/or quantify the concentration of the analyte in the sample. For example, the amount of immobilized probe conjugate can be quantified by observing the drop in the amount of free probe conjugate that is transferred to the detection chamber.

In yet another embodiment, the immobilized binding site 44 can be the target antigen and the probe conjugate 50 can comprise an enzyme coupled to an antibody that is capable of binding to the analyte of interest. Preferably the immobilized binding site and probe conjugate are position separately in the reaction chamber to prevent or reduce any reaction prior to the introduction of sample.

When a sample containing the target antigen fills the reaction chamber, the target antigen in the sample can bind to the probe conjugate (antibody), reducing the amount of probe conjugate that binds to the immobilized binding site (antigen). The presence or absence of the target antigen therefore changes the amount of probe conjugate bound in the reaction chamber. The fraction immobilized can be used to detect the presence and/or quantify the concentration of the analyte in the sample. For example, the amount of immobilized probe conjugate can be quantified by observing the drop in the amount of free probe conjugate that is transferred to the detection chamber.

In one aspect, the immobilized binding sites and/or the probe conjugate are bound to beads. For example, the immobilized binding sites (antigen) can be positioned on beads that are dried on one surface of the reaction chamber and the probe conjugate (antibody) can be dried on another surface of the reaction chamber. The beads can be magnetic beads that are prevented from leaving the reaction chamber by means of a magnetic field. When sample fills the reaction chamber, antigen in the sample binds to the antibody of the probe conjugate and prevents the immobilized binding site (antigen) from the binding with the probe conjugate, thus leaving the probe conjugate free to be transferred to the detection chamber.

As mentioned above, beads can have characteristics such that they will remain in the reaction chamber when the sample transfers to the detection chamber. For example, the para-magnetic beads can be aligned with field lines of an applied magnetic field such that they are held by the field and thus prevented from being transferred with the sample to detection chamber. The magnetic field can be applied by any suitable device such as an electromagnet or, in an alternative embodiment when it is desired to minimize power consumption, the magnetic field can be applied by a permanent magnet. In one embodiment the magnet or magnets could be placed so that they are closer to the location in the reaction chamber of the probe conjugate and further from the location in the reaction chamber of the para-magnetic beads. With this arrangement, the beads will tend to move towards, and mix with, the probe conjugate under the influence of the magnetic field. Once the beads have moved to and mixed with the probe conjugate, the applied magnetic field will tend to prevent the beads from moving to locations with a lower concentration of magnetic field lines, thus the beads will be immobilized in the reaction chamber by the magnetic field.

Regardless of the configuration of the immobilized binding site and the probe conjugate, after the sample reactions within the reaction chamber, the reacted sample is moved to the detection chamber. This can occur at a predetermined time after the sample is introduced into the reaction chamber. For example, the predetermined time can be set such that there is sufficient time for substantially all of the probe conjugate to bind. In one aspect, the residence time of the sample in the reaction chamber can be calculated by a user manually. Alternatively, the residence time can be calculated electronically by a meter in electrical contact with the sensor.

In one embodiment, the residence time of the sample in the reaction chamber is monitored via electrodes. For example, in the sensor of FIGS. 1 and 2 when sample fills the reaction chamber 22, a small portion of the detection chamber 28 at its opening 38 into the reaction chamber 22 will be wet by sample. The electrodes 52 and 54 can be placed in the detection chamber 28, such that at least a portion of each electrode 52 and 54 is contacted by the sample during the filling of the reaction chamber 22, such that the presence of the sample will bridge the electrodes 52 and 54 and create an electrical signal which can be used to trigger the timing device. In another embodiment, illustrated in the sensor of FIGS. 3 and 4, a separate electrically contact (contact 103), used in conjunction with the lower electrode and contact area 101, can detect the presence of sample in the reaction chamber.

A predetermined time after the sample has entered the reaction chamber, the immunological reaction phase of the test is deemed to be completed. The vent 30, 130 can then be opened to the atmosphere. For example, a solenoid activated needle in the meter may be used to pierce layer the vent. The piercing can be automatically performed by the meter or manually by the user, e.g., the user inserts a needle through the layer(s) covering the vent.

Optionally disposed in the detection chamber 28, 128 are dried reagents 64 comprising an enzyme substrate and a mediator, capable of reacting with the enzyme part of the probe conjugate to produce a detectable signal. The enzyme substrate and mediator, if present, can be of sufficient amount such that the rate of reaction of any enzyme present with the enzyme substrate is determined by the amount of enzyme present. For instance, if the enzyme were glucose oxidase or glucose dehydrogenase, a suitable enzyme mediator and an enzyme substrate such as glucose (if not already present in the sample) would be disposed into detection chamber 28, 128. In one alternative embodiment sufficient glucose would be disposed into the detection chamber 28, 128 such that any variations in the level of glucose in the incoming sample did not significantly alter the enzyme reaction rate. Buffer may also be included to help adjust the pH of the sample in detection chamber 28, 128. In one embodiment ferricyanide is a suitable mediator. Other suitable mediators include dichlorophenolindophenol and complexes between transition metals and nitrogen-containing heteroatomic species. Additionally, a second mediator such as phenazine ethosulphate, and/or 2,3 dimethoxy-5-methyl-p-benzoquinone, which promotes a more efficient transfer of electrons from the enzyme to the ferricicyanide species can be added. The enzyme substrate, mediator, second mediator, and buffer reagents 64 can be present in sufficient quantities such that the rate of reaction of the enzyme with the enzyme substrate is limited by the concentration of the enzyme present.

When the detection chamber 28, 128 is filled, the reagents 64 dissolve into the sample. The enzyme component of the probe conjugate reacts with the enzyme substrate and the mediator to produce reduced mediator. This reduced mediator is electrochemically oxidized at an electrode acting as an anode in the detection chamber 28, 128 to produce an electrical current. In one embodiment, the rate of change of this current with time is used as an indicator of the presence and amount of enzyme that is present in the reacted sample. If the rate of change of current is less than (or more than) a predetermined threshold value, then it indicates that no significant amount (or a significant amount) of probe conjugate 50 is present in the reacted sample, indicating the presence (or lack) of antigen present in the original sample. Conversely, the rate of change of a current more than (or less than) a predetermined threshold value can be used to indicate the lack (or presence) of an antigen in the sample. In one embodiment, the rate of change of the current is used to give a measure of the relative amount of antigen initially present in the sample. For example, the rate of change of current can be used to determine probe conjugate concentration, which can be correlated to the concentration of the antigen in the sample.

Use of Melittin as a Probe.

In one embodiment, a probe-linked antigen comprising an antigen-melittin complex can be dried on a wall of the reaction chamber, as described above. The detection chamber can contain a mediator comprising ferrocyanide in liposomes or lipid vesicles. If the antigen-melittin complex reaches the liposomes, they will burst and release the ferrocyanide. This leads to a rapid amplification of the signal, i.e., a small amount of free antigen competes with the antigen-melittin complex for binding sites on the antibodies and results in a large concentration of ferrocyanide.

Use of Horse Radish Peroxidase and Alkaline Phosphatase in Electrochemical Assays.

Conventional ELISAs use horse radish peroxidase (HRP) or alkaline phosphatase (AP) as the enzymes in a calorimetric assay. However, substrates have been developed which allow both these enzymes to be used in an electrochemical assay. In this embodiment, AP can be used with p-aminophenyl phosphate and HRP can be used with tetrathiafulvalene.

The following non-limiting example is illustrative of the principles and practice of this invention. Numerous additional embodiments within the scope and spirit of the invention will become apparent to those skilled in the art.

EXAMPLE

An exemplary immunosensor assay for human C Reactive protein in whole blood using magnetic beads coated with Human C reactive protein was performed. C reactive protein (CRP) was covalently attached to 1.5 micron Carboxylated BioMag magnetic beads (Cat no BM570; Bangs Laboratories, Indianapolis In, USA). 21.9 mg of beads (1 ml) were washed 4 times with 50 mM MES (Morpholinoethanesulphonic acid (Sigma-Aldrich, St Louis, Mo. USA) buffer pH 5.2 by incubating with this buffer and using a magnet to concentrate the beads on the side of the tube and after 2 min remove the buffer with a transfer pipette. After the fourth wash, the beads were suspended in a final volume of 0.34 ml SOM MES. 40 ul of 100 mg/ml EDAC (Sigma, St Louis, Mo. USA) was added and after 5 minutes added 450 ug of CRP in Phosphate buffered saline (Hytest, Turku Finland) was added. Beads were allowed to incubate for a further 30 min at room temperature. Unbound CRP was removed by using a magnet to concentrate the beads as described above. The beads were then blocked by incubating for 30 min in a buffer containing 20 mM Tris(2-amino-2-hydroxymethyl)-1,3 propandiol), 0.15 M Sodium Chloride pH 7.4 (TBS) and 1 mg/ml Bovine serum albumin (BSA) (Sigma-Aldrich, St Louis, Mo. USA) and then washed four times in the same buffer using magnetic concentration. Beads were stored in TBS/BSA containing 0.05% sodium azide (Signa-Aldrich, St Louis, Mo. USA).

Glucose Dehydrogenase/Antibody Conjugate.

Conjugation of Glucose dehydrogehase (Recombinant *E. coli* enzyme; Kiikoman Corporation, Chiba, Japan) GDH and monoclonal antibody 4C28 clone C2 (Hytest; Turku Finland) was accomplished using the reagent MBS (M-Maleimidobenzoyl-N-Hydroxysuccinimide ester) based on the method described by 0 Sullivan et al. (Anal. Biochem. 100 100-108 1979).

In this example MBS was reacted with amino groups on GDH and the MBS-GDH intermediate was purified. Then maleimide groups on the SMCC-GDH complex were reacted with free sulphydryl groups on the hinge region of the antibody introduced by reaction with the reducing reagent cysteamine HCl.

1. Reduction of IgG Hinge Region Disulphides

Six mg of cysteamine HCl (Sigma-Adrich, St Louis, Mo. USA) was incubated for 90 minutes at 37° C. with 1 ml of a solution containing 2 mg/ml Mab C2 in a buffer containing 0.1M Sodium phosphate pH 7.4; 0.15 M NaCl and 2.5 mM EDTA (reaction buffer). The reaction was terminated by applying the mixture to a desalting column (PD-10 Amerscham) equilibrated in reaction buffer and elution continued in the same buffer. One-half milliliter fractions were collected and the three fractions containing the most protein were pooled. This material was reacted with the maleimide activated enzyme as soon as it was pooled. The protein concentration was determined assuming an absorbance at 280 nm of 1.35 for a 1 mg/ml solution of antibody C2.

2. Maleimide Activation of the Enzyme

At the same time 2 mg of GDH was dissolved in 1.0 ml of the reaction buffer and 50 ul of a solution of containing 7.6 mg/ml MBS (Pierce Rockford Ill. USA) in DMSO was added and allowed to incubate for 30 min at 37° C. The reaction was terminated by applying the mixture to a desalting column (PD-10; Amerscham) equilibrated in the reaction buffer and elution continued in the same buffer. One-half milliliter fractions were collected and the three fractions containing the most protein were pooled.

3. Conjugation of Antibody to Enzyme

The reduced IgG and maleimide reacted GDH were mixed together in the ratio of 1 mg of Ab to 0.9 mg of GDH and incubated overnight at 4° C. The reaction was terminated by adding 6 mg of cysteamine HCl and allowing to incubate for a further 15 min at room temperature and then applying 1.5 ml aliquots to separate desalting columns equilibrated with and continuing the elution in a buffer containing 20 mM Tris and 0.15 M Sodium Chloride pH 7.4 (TBS). The three 0.5 ml fractions containing the highest concentration of protein from each column were pooled. Calcium chloride was added to a final concentration of 1 mM, sodium azide to a final concentration of 0.1% and PQQ to a final concentration of 0.05 mg/ml. Conjugate was stored at 4° C. prior to use.

Conventional Immunoassay for C Reactive Protein.

The CRP levels in samples were also determined by conventional enzyme immunoassay. All incubations were carried out at room temperature.

The wells of Immulon 11 microplates were coated with 50 ul of a 10 ug/ml monoclonal antibody C2 in TBS buffer for 60 min at room temperature. Unbound antibody was removed by inversion and tapping the plate and then washing the wells four times with 200 ul of TBS buffer containing 0.1% TWEEN 20 (Polyoxyethylenesorbitan monlaurate; Sigma-Adrich, St Louis, Mo. USA).

Then 50 ul of known standards, or sample containing unknown amounts of CRP was added, usually diluted 100-1000 fold in TBS/TWEEN, to each well and allowed to incubate for a further hour. Unbound antigen was then removed by the washing procedure described above. Next 50 ul of a 220 ng/ml solution of biotinylated C6 antibody in TBS/TWEEN was added and allowed to incubate for further 60 min. After washing away unbound second antibody, 50 ul of a 1/1000 dilution of neutravidin-horseradish peroxidase was added (Pierce Rockford Ill. USA) and the reaction allowed to proceed for a further 15 min. Finally, after washing to remove unbound enzyme, bound enzyme was detected by the addition of ABTS substrate (Pierce Rockford Ill. USA).

Biotinylation of antibody C6 was carried out by the following method. Two milligrams of monoclonal antibody C6 (Hytest, Turku Finland) were dissolved 1 ml of 50 mM Sodium bicarbonate and reacted with 29 ul of 1 mg/ml solution of biotin N Hydroxysuccinimide ester (Pierce) in Dimethyl sulphoxide (Sigma). The reaction was allowed to proceed for 30 min with occasional shaking. The reaction was terminated by applying the mixture to a desalting column (PD-10; Amerscham) equilibrated in 20 mM Tris (2-amino-2-hydroxymethyl)-1,3 propandiol), 0.15 M Sodium Chloride pH 7.4 (TBS) and elution continued in the same buffer. One-half milliliter fractions were collected and the three fractions containing the most protein were pooled. The material was stored at 4° C. Protein concentration was determined by absorbance at 280 nm assuming a 1 mg/ml solution of C6 had an absorbance of 1.2.

Sensor Strips

Sensor strips were constructed as following:

1) The electrode webs consisted of 178 um thick Melinex which was sputter coated with a layer of gold. The surface resistance of the gold coating was 8-12 ohms/sq.
2) The electrode was coated with a solution of 0.3 mM 2-mercaptoethanesulphonic acid for 20 seconds and then dried with a jet of air. This procedure keeps the electrode hydrophilic and reduces fouling by air-borne hydrocarbons and other contaminants.
3) A web process was used to dry stripes of chemistry (e.g., reagents described above) onto the electrode. The web was transported past a fixed razor blade which placed a scratch on the surface and helped to define the area of the working electrode. The web was then transported past two blunt-tipped stainless steel pipetting needles linked to a syringe pump which deposited:
   the electrochemical reagent (ferricyanide, glucose, etc.) so that it overlapped the scratch, and
   the antibody-enzyme conjugate on the other side of the scratch about 1-2 mm away from the electrochemical reagent.
4) The chemistry stripes were dried with infrared dryers and hot air at 50 degrees C.
5) The reaction and detection chamber shapes were kiss-cut into the spacer using a rotary crush-cut tool.
6) The spacer was laminated onto the electrode in such a way that the antibody-enzyme conjugate was in the reaction chamber and the electrochemical reagent was in the detection chamber.
7) The filling chamber was punched into the bi-laminate using a male/female die set.
8) Antigen bound to paramagnetic beads was striped onto a separate electrode film.
9) The electrode with the paramagnetic beads was then bonded to the bi-laminate from step (6) in such a way that the antigen-bead stripe was opposite the antibody-enzyme conjugate in the reaction chamber.
10) The vent hole in each sensor was punched into the tri-laminate using a male/female die set.
11) The vent holes and the open side of the filling chamber were covered with "magic tape" (3M).
12) The tri-laminate web was singulated to yield working sensors.

Electrochemical Detection of GDH.

The solution contained 5 mg/ml 2,3 Dimethoxy-5-methyl 1,4 benzoquinone (Adrich, Wis. USA) 326 mg/ml potassium ferricyanide 400 mM glucose in a buffer containing 0.26 mg/ml citraconic acid (Sigma) and 13.3 mg/ml Di potassium citraconate.

Conjugate

Solution contained 400 ug/ml GDH was diluted to 100 ug/ml in a solution containing 1 mM Calcium chloride, 10 mg/ml BSA 0.26 mg/ml citraconic acid, 13.3 mg/ml Di potassium citraconate, and 10 mg/ml sucrose.

Magnetic Beads

Solution contained 5 mg/ml CRP coated beads, 100 mg/ml sucrose, 1 mM Calcium chloride, 0.26 mg/ml citraconic acid, and 13.3 mg/ml Di potassium citraconate Sample Preparation Normal heparainized whole blood with an Hemocrit of 42% and plasma concentration of 1 ug/ml CRP was used for the following experiment. (CRP blood), To 10 ul of whole blood 10 ul of a solution of 2.5 mg/ml CRP in phosphate buffed saline was added. 10 ul of phosphate buffed saline was added to another 100 ul sample as a control.

Test Procedure

Approximately 5 ul of blood was added to the filling chamber (feature 107 of FIG. 3). The blood flowed to fill filling chamber 107 and reaction chamber 122 and stopped near the entrance to detection chamber 128. The blood dissolved the conjugate from the wall of reaction chamber 122 and allowed interaction with the magnetic beads which were drawn to the bottom of reaction chamber 122 by the presence of a magnet under the reaction chamber 122. In the absence of added CRP the majority of conjugate will be able to bind the magnetic beads.

After incubation for 40 seconds the vent hole 130 in FIG. 3 was punctured. This allowed blood together with any unbound GDH conjugate to flow past the scratch line (106) into the detection chamber where measurement of the electrical current flowing between the electrodes in the detection chamber was initiated. The current generated by the presence of GDH in the detection chamber was measured over the next 45 s. The results below are for six replicate samples of the control blood or blood containing 250 ug/ml CRP. They show the current in PA at 5 seconds and 45 seconds after the detection chamber 128 was filled. The difference in the current between 5 and 45 seconds was used as a measure of the CRP concentration in the sample.

|  | Control sample | | | With 250 ug/ml CRP added | | |
| --- | --- | --- | --- | --- | --- | --- |
|  | 5 sec | 45 sec | Difference | 5 sec | 45 sec | Difference |
|  | 19.01 | 27.72 | 8.71 | 24.26 | 40.8 | 16.54 |
|  | 16.99 | 26.45 | 9.46 | 20.32 | 37.25 | 16.93 |
|  | 20.05 | 28.41 | 8.36 | 26.39 | 47.25 | 20.86 |
|  | 18.81 | 31.1 | 12.29 | 25.12 | 50.44 | 25.32 |
|  | 16.75 | 24.0 | 7.05 | 20.41 | 39.09 | 18.68 |
|  | 22.94 | 34.22 | 11.28 | 17.93 | 35.77 | 17.84 |
| Avg. |  |  | 9.525 |  |  | 19.36 |
| Std dev. |  |  | 1.77 |  |  | 1.55 |

As shown in the table above, there was a significant difference in the rate of change of current between the control sample and the sample to which 250 μg ml CRP was added. The immunosensor was thus able to detect the presence of CRP within the sample.

One skilled in the art will appreciate fiber features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A biosensor for use in detecting a target analyte in a fluid sample, the biosensor comprising:
   a reaction chamber including an immobilized binding site and a probe conjugate, wherein the probe conjugate comprises a binding partner adapted to bind to the immobilized binding site, wherein the immobilized binding site is positioned on at least one magnetic bead, wherein the immobilized binding site and the probe conjugate are positioned on different surfaces of the reaction chamber;
   a detection chamber including electrodes for detecting an electrochemical reaction in the detection chamber; and
   a fluid passageway between the reaction chamber and the detection chamber, wherein the presence or absence of the target analyte in the fluid sample results in a change in the amount of the probe conjugate bound in the reaction chamber, the change detectable with an electrochemical reaction in the detection chamber.

2. The biosensor of claim 1, wherein the immobilized binding site is an antigen and the binding partner is an antibody.

3. The biosensor of claim 1, wherein the immobilized binding site is an antibody and the binding partner is an antigen.

4. The biosensor of claim 1, further comprising a filling chamber adapted to be filled by capillary action, wherein the filling chamber is proximal to and in fluid communication with the reaction chamber.

5. The biosensor of claim 4, wherein the capillary dimension of the reaction chamber is smaller in size than that of the filling chamber.

6. The biosensor of claim 1, wherein the detection chamber includes a vent.

7. The biosensor of claim 6, wherein the vent can be opened by piercing an outer layer of the biosensor.

8. The biosensor of claim 6, wherein the vent can be opened by removing a portion of an outer layer of the biosensor.

9. The biosensor of claim 6, wherein the vent can be opened by tearing along a perforation.

10. The biosensor of claim 1, wherein the reaction chamber includes an opening to the atmosphere.

11. The biosensor of claim 1, further comprising a magnet.

12. The biosensor of claim 11, wherein the magnet is disposed so as to move the at least one magnetic bead to be in intimate contact with the probe conjugate after the fluid sample has been introduced into the reaction chamber.

13. The biosensor of claim 1, wherein the probe conjugate comprises an enzyme.

14. The biosensor of claim 13, further comprising a mediator and a substrate for the enzyme.

15. A method of detecting a target analyte in a fluid sample, the method comprising the steps of:
  delivering a sample to the biosensor of claim 1;
  allowing a reaction to proceed in the reaction chamber between the immobilized binding site and the probe conjugate; and
  moving the sample into the detection chamber and electrochemically detecting the level of probe conjugate, wherein the presence of the target analyte in the sample results in an increase or a decrease in the amount of probe conjugate detected in the detection chamber.

16. The method of claim 15, wherein the immobilized binding site includes a target antigen and the probe conjugate includes an antibody adapted to bind to the target antigen.

17. The method of claim 15, wherein the probe conjugate includes an enzyme.

18. The method of claim 15, wherein the sample is moved from the reaction chamber to the detection chamber via capillary action.

19. The method of claim 15, wherein the step of moving the sample includes opening a vent.

20. The method of claim 15, further comprising the step of quantifying the amount of target antigen in the sample based electrical signals received from the detection chamber.

21. A method of manufacture of the biosensor of claim 4, the method comprising the steps of:
  providing a first layer;
  removing a section of the first layer to form the filling chamber, the reaction chamber, and the detection chamber;
  providing a second layer;
  mounting a first side of the second layer to a first side of the first layer;
  removing a section of the second layer extending over the filling chamber, in substantial registration with the filling chamber, the second layer further extending over the reaction chamber and the detection chamber;
  providing a third layer;
  mounting a first side of the third layer to a second side of the first layer, the third layer extending over the filling chamber, the reaction chamber and the detection chamber;
  mounting a first side of a sealing layer to a second side of the second layer, whereby the layers comprising the first layer, the second layer, the third layer and the sealing layer form a strip having a plurality of exterior surfaces;
  forming a passageway extending through an exterior surface of the strip into the detection chamber so as to form a detection chamber vent;
  mounting a layer over the passageway opening to the exterior surface of the strip so as to close the detection chamber vent; and
  placing the immobilized binding site and the probe conjugate within the reaction chamber.

22. A method of manufacture of the biosensor of claim 4, the method comprising the steps of:
  providing a first layer and a second layer;
  mounting at least one section of the first layer on a first surface of the second layer to the filling chamber, the reaction chamber, and the detection chamber;
  providing a third layer;
  mounting a first side of the third layer to a second side of the first layer, the third layer extending over the filling chamber, the reaction chamber and the detection chamber;
  forming a passageway extending through an exterior surface of the strip into the detection chamber so as to form a detection chamber vent;
  mounting a layer over the passageway opening to the exterior surface of the strip so as to close the detection chamber vent; and
  placing the immobilized binding site and the probe conjugate within the reaction chamber.

23. A method of manufacture of the biosensor claim 4, the method comprising the steps of:
  providing a first layer;
  providing a second layer;
  mounting a first side of the second layer to a first side of the first layer;
  providing a third layer;
  mounting a first side of a third layer to a second side of the first layer;
  removing the section of the first layer to form a filling chamber;
  removing the section of the first layer to form a reaction chamber;
  removing the section of the first layer to form a detection chamber, whereby the reaction chamber and the detection chamber are in fluid communication with the filling chamber;

forming a passageway extending through an exterior surface of the strip into the detection chamber so as to form a detection chamber vent;

mounting a layer over the passageway opening to the exterior surface of the strip so as to close the detection chamber vent; and placing the immobilized binding site and the probe conjugate within the reaction chamber.

24. A biosensor for use in detecting a target analyte in a fluid sample, the biosensor comprising:

a reaction chamber including an immobilized binding site and a probe conjugate, wherein the probe conjugate comprises a binding partner adapted to bind to the immobilized binding site, wherein the immobilized binding site is positioned on at least one magnetic bead, wherein the magnetic bead remains in the reaction chamber, wherein the immobilized binding site and the probe conjugate are positioned on different surfaces of the reaction chamber;

a detection chamber including electrodes for detecting an electrochemical reaction in the detection chamber; and a fluid passageway between the reaction chamber and the detection chamber, wherein the presence or absence of a target analyte in the fluid sample results in a change in the amount of probe conjugate bound in the reaction chamber, the change detectable with an electrochemical reaction in the detection chamber.

* * * * *